(12) United States Patent
Burk et al.

(10) Patent No.: US 9,573,926 B2
(45) Date of Patent: Feb. 21, 2017

(54) AMIDOALKYLENYL AND AMIDOARYL ESTERS, COMPOSITIONS THEREOF, AND METHODS FOR THEIR USE

(71) Applicant: Allergan, Inc., Irvine, CA (US)

(72) Inventors: Robert M. Burk, Laguna Beach, CA (US); Yariv Donde, Dana Point, CA (US); Jeremiah H. Nguyen, La Puente, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

(21) Appl. No.: 14/719,750

(22) Filed: May 22, 2015

(65) Prior Publication Data

US 2015/0336924 A1 Nov. 26, 2015

Related U.S. Application Data

(60) Provisional application No. 62/002,062, filed on May 22, 2014.

(51) Int. Cl.
| | | |
|---|---|---|
| *A01N 65/00* | (2009.01) | |
| *A01N 43/06* | (2006.01) | |
| *A61K 31/38* | (2006.01) | |
| *C07D 333/38* | (2006.01) | |
| *A61K 9/00* | (2006.01) | |

(52) U.S. Cl.
CPC ........... *C07D 333/38* (2013.01); *A61K 9/0048* (2013.01)

(58) Field of Classification Search
USPC .................................................. 514/448, 71
See application file for complete search history.

(56) References Cited

U.S. PATENT DOCUMENTS

| | | | |
|---|---|---|---|
| 4,166,452 A | 9/1979 | Generales, Jr. | |
| 4,256,108 A | 3/1981 | Theeuwes | |
| 4,265,874 A | 5/1981 | Bonsen et al. | |
| 7,592,366 B2 | 9/2009 | Old et al. | |
| 7,947,732 B2 * | 5/2011 | Old .................. | C07D 333/16 514/336 |
| 2010/0210689 A1 | 8/2010 | Old et al. | |
| 2014/0057975 A1 | 2/2014 | Im et al. | |

OTHER PUBLICATIONS

Berge, Stephen, et al., Pharmaceutical Salts, J. Pharmaceutical Sciences 1977, 66: 1-19 (1).
Osol, Arthur, et al., Remington's Handbook, 1980, 16th Ed., pp. I-IX.
Silverman, Richard, Prodrugs & Drug Delivery Systems, Organic Chemistry of Drug Design & Drug Action, 2004, Chap. 8, pp. 497-557.
Stahl, P. Heinrich, et al., Handbook of Pharmaceutical Salts, Helvetica Chimica Acta—Zürich, 2002, 329-345.
International Search Report & Written Opinion mailed on Sep. 17, 2015 for PCT/US15/32264 filed May 22, 2015 in the name of Allergan, Inc.

* cited by examiner

*Primary Examiner* — Marcos Sznaidman
(74) *Attorney, Agent, or Firm* — Jonathon Bass

(57) ABSTRACT

The invention provides ester compounds for treating ophthalmic diseases. The esters of the invention are particularly advantageous due to their stability in aqueous solutions.

20 Claims, No Drawings

AMIDOALKYLENYL AND AMIDOARYL ESTERS, COMPOSITIONS THEREOF, AND METHODS FOR THEIR USE

CROSS REFERENCE TO RELATED APPLICATIONS

This application is a non-provisional application which claims the benefit of U.S. provisional application 62/002,062, filed on May 22, 2014 which is incorporated by reference herein in its entirety.

FIELD

The present disclosure relates generally to compounds and methods for the treatment of ocular disorders, and more particularly to the use of the compounds disclosed herein for the treatment of glaucoma and ocular hypertension.

BACKGROUND

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Therefore, there is a need for compounds for the treatment of ophthalmic diseases such as glaucoma, and for related compositions and methods.

SUMMARY OF THE INVENTION

Provided herein are compounds for treating ophthalmic diseases. The esters disclosed herein are particularly advantageous due to their stability in aqueous solutions. As such, the compounds of the invention can be readily incorporated into stable aqueous formulations useful for treating certain ocular conditions. In one embodiment, provided herein are compounds of formula (I):

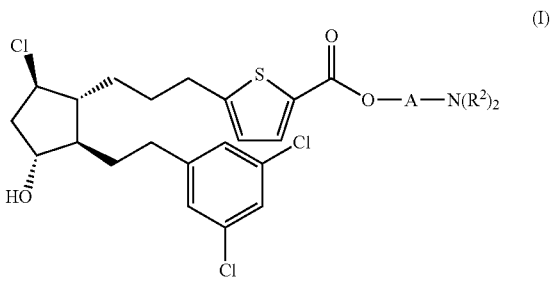

or pharmaceutically acceptable salts thereof, wherein:
A is $(C(R^1)_2)_n$, aryl, or heteroaryl containing 1 to 4 heteroatoms selected from the group consisting of N, O and S;
each $R^1$ is independently selected from the group consisting of H and —$CH_2OH$;
each $R^2$ is independently selected from the group consisting of H, $C_1$ to $C_6$ alkyl, $C_1$ to $C_6$ alkylhydroxy, and $C(O)R^3$;
each $R^3$ is independently $C_1$ to $C_6$ alkyl; and
n is 1 to 6.

In another embodiment, there are provided pharmaceutical compositions including at least one compound of the invention, the compound being present alone or in combination with one or more pharmaceutically acceptable excipients.

In another embodiment, there are provided compositions including at least one compound of the invention, wherein the composition is a liquid which is ophthalmically acceptable.

In another embodiment there are provided methods for the treatment of an ophthalmic disease. In some embodiments, the disease is selected from the group consisting of glaucoma, ocular hypertension, and macular degeneration. Such methods can be performed, for example, by administering to a subject in need thereof a therapeutically effective amount of at least one compound of the invention.

In another embodiment there are provided methods for reducing intraocular pressure. Such methods can be performed for example, by administering to a subject in need thereof a therapeutically effective amount of at least one compound of the invention.

In a further embodiment there are provided methods for reducing corneal thickening. Such methods can be performed for example, by administering to a subject in need thereof a therapeutically effective amount of at least one compound of the invention.

DETAILED DESCRIPTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation.

As used herein, "alkyl" refers to straight or branched chain hydrocarbyl groups having from 1 up to about 100 carbon atoms. Whenever it appears herein, a numerical range, such as "1 to 100" or "$C_1$-$C_{100}$", refers to each integer in the given range; e.g., "$C_1$-$C_{100}$ alkyl" means that an alkyl group may comprise only 1 carbon atom, 2 carbon atoms, 3 carbon atoms, etc., up to and including 100 carbon atoms, although the term "alkyl" also includes instances where no numerical range of carbon atoms is designated. "Substituted alkyl" refers to alkyl moieties bearing substituents including alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, lower alkylamino, lower alkyldiamino, amido, azido, —C(O)H, —C(O)$R_7$, —CH$_2$O$R_7$, —C(O)—, —C(O)—, —S—, —S(O)$_2$—, —OC(O)—O—, wherein $R_7$ is H or lower alkyl, acyl, oxyacyl, carboxyl, carbamate, sulfonyl, sulfonamide, sulfuryl, and the like. In some embodiments, "alkyl" refers to alkyl moieties having 1 to 6 carbon atoms (e.g. "lower alkyl").

As used herein, "alkylene" or "alkylenyl" refers to a divalent alkyl moiety. In other words, such a moiety has two points of attachment to the rest of the molecule (e.g. —CH$_2$CH$_2$—).

As used herein, "alkenyl" refers to straight or branched chain hydrocarbyl groups having at least one carbon-carbon double bond, and having in the range of about 2 up to about 100 carbon atoms, and "substituted alkenyl" refers to alkenyl groups further bearing one or more substituents as set forth above. In some embodiments, "alkenyl" refers to alkenyl moieties having 2 to 6 carbon atoms (e.g. "lower alkenyl").

As used herein, "alkynyl" refers to straight or branched chain hydrocarbyl groups having at least one carbon-carbon triple bond, and having in the range of about 2 up to about 100 carbon atoms, and "substituted alkynyl" refers to alkynyl groups further bearing one or more substituents as set forth above. In some embodiments, "alkynyl" refers to alkynyl moieties having 2 to 6 carbon atoms (e.g. "lower alkynyl").

As used herein, "alkylhydroxy" refers to straight or branched chain alkyl groups substituted with one or more hydroxyl (—OH) groups. Examples of alkylhydroxy groups include, but are not limited to, —CH$_2$OH, and others identifiable to a skilled person. In some embodiments, the alkylhydroxy group contains 1 to 6 carbon atoms (e.g. "lower alkylhydroxy").

As used herein, "cycloalkyl" refers to cyclic (i.e., ring-containing) alkyl moieties typically containing in the range of about 3 up to about 8 carbon atoms, and "substituted cycloalkyl" refers to cycloalkyl groups further bearing one or more substituents as set forth above.

As used herein, "aryl" refers to aromatic groups having in the range of 5 up to 14 carbon atoms and "substituted aryl" refers to aryl groups further bearing one or more substituents as set forth above. Exemplary aryl groups include, for example, phenyl, naphthyl, and others identifiable to a skilled person upon a reading of the present disclosure.

As used herein, "heteroaryl" refers to aromatic moieties containing one or more heteroatoms (e.g., N, O, S, or the like) as part of the ring structure and having in the range of 5 up to 14 total atoms in the ring structure (i.e., carbon atoms and heteroatoms). Exemplary heteroaryl groups include, for example, thienyl, furyl, pyrrolyl, pyridyl, and others identifiable to a skilled person upon a reading of the present disclosure. In some embodiments, the heteroaryl group is substituted. Examples of substituents include, but are not limited to, those listed above. In some embodiments, the substituted heteroaryl is mono-, di-, tri- or tetra-substituted. In some embodiments, the heteroaryl is unsubstituted.

As used herein, "heterocyclic" refers to non-aromatic cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As used herein, "halogen" or "halide" refers to fluoride, chloride, bromide or iodide. "Fluoride, chloride, bromide or iodide" may also be referred to as "fluoro, chloro, bromo, or iodo".

Certain eicosanoids and their derivatives can be used in glaucoma management. Eicosanoids and derivatives include numerous biologically important compounds such as prostaglandins and their derivatives. Prostaglandins can be described as derivatives of prostanoic acid. Prostanoic acid has the following structural formula:

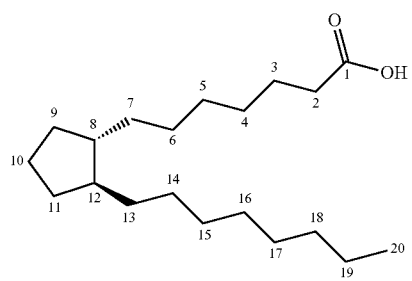 [SMILES: CCCCCCCC[C@H]1CCC[C@@H]1CCCCCCC(=O)O]

Various types of prostaglandins are classified by the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ (PGE$_1$), prostaglandin $E_2$ (PGE$_2$)], and on the configuration of the substituents on the alicyclic ring indicated by α or β [e.g. prostaglandin $F_{2\alpha}$ (PGF$_{2\alpha}$)]. Changes in the substituents of carbons 9, 10, and 11 can often influence the activity and selectivity of these compounds at the different prostaglandin receptors. Other compounds having more remote structures from natural prostaglandins can also have activity at prostaglandin receptors.

Provided herein are compounds of formula (I):

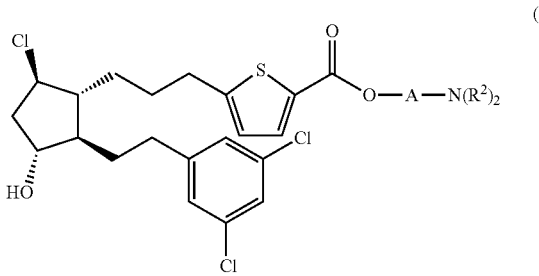

(I)

wherein:
A is $(C(R^1)_2)_n$, aryl, or heteroaryl containing 1 to 4 heteroatoms selected from the group consisting of N, O and S;
each $R^1$ is independently selected from the group consisting of H and $-CH_2OH$;
each $R^2$ is independently selected from the group consisting of H, $C_1$-$C_6$ alkyl; $C_1$-$C_6$ alkylhydroxy, and $C(O)R^3$;
each $R^3$ is independently $C_1$ to $C_6$ alkyl; and
n is 1 to 6.

In some embodiments of formula (I), each $R^1$ is H.
In some embodiments of formula (I), each $R^1$ is $-CH_2OH$.
In some embodiments of formula (I), one $R^2$ is H the other $R^2$ is $C(O)R^3$. In some embodiments of formula (I), one $R^2$ is H, the other $R^2$ is $C(O)R^3$, and $R^3$ is methyl.
In some embodiments of formula (I), one $R^2$ is H or alkylhydroxy and the other $R^2$ is $C(O)R^3$. In some embodiments of formula (I), one $R^2$ is $C_2$ alkylhydroxy, the other $R^2$ is $C(O)R^3$, and $R^3$ is methyl.
In some embodiments of formula (I), $R^3$ is methyl.
In some embodiments of formula (I), A is $(C(R^1)_2)_n$ and n is 1. In some embodiments of formula (I), A is $(C(R^1)_2)_n$ and n is 2. In some embodiments of formula (I), A is $(C(R^1)_2)_n$ and n is 3.
In some embodiments of formula (I), A is $(C(R^1)_2)_n$ and each $R^1$ is H. In some embodiments of formula (I), A is $(C(R^1)_2)_n$, each $R^1$ is H, and n is 1. In some embodiments of formula (I), A is $(C(R^1)_2)_n$, each $R^1$ is H, and n is 2. In some embodiments of formula (I), A is $(C(R^1)_2)_n$, each $R^1$ is H, and n is 3.
In some embodiments of formula (I), A is $(C(R^1)_2)_n$ and each $R^1$ is $-CH_2OH$. In some embodiments of formula (I), A is $(C(R^1)_2)_n$, each $R^1$ is $-CH_2OH$, and n is 1. In some embodiments of formula (I), A is $(C(R^1)_2)_n$, each $R^1$ is $-CH_2OH$, and n is 2. In some embodiments of formula (I), A is $(C(R^1)_2)_n$, each $R^1$ is $-CH_2OH$, and n is 3.
In some embodiments of formula (I), A is aryl. In some embodiments, aryl is phenyl. In some embodiments of formula (I), A is aryl, aryl is phenyl, one $R^2$ is H or alkylhydroxy and the other $R^2$ is $C(O)R^3$. In some embodiments of formula (I), A is aryl, aryl is phenyl, one $R^2$ is H or alkylhydroxy, the other $R^2$ is $C(O)R^3$, and $R^3$ is methyl. In some embodiments of formula (I), A is aryl, aryl is phenyl, one $R^2$ is H, the other $R^2$ is $C(O)R^3$, and $R^3$ is methyl. In some embodiments of formula (I), A is aryl, aryl is phenyl, one $R^2$ is $C_2$ alkylhydroxy, the other $R^2$ is $C(O)R^3$, and $R^3$ is methyl.

The compounds of formula (I) as provided herein are esters which confer the advantage of increased stability in aqueous solution relative to their corresponding carboxylic acids. The esters of the invention may be considered "prodrugs" of the corresponding carboxylic acids. "Prodrug" refers to a compound which converts to a therapeutically active compound after administration and is used herein as it is generally understood in the art. Conversion of the prodrug into an activated form may occur by hydrolysis of an ester group or some other biologically labile group. Generally, but not necessarily, a prodrug is inactive or less active than the therapeutically active compound into which it is converted. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject.

In some embodiments, provided herein are pharmaceutical compositions including at least one compound of the invention, the compound being present alone or in combination with one or more pharmaceutically acceptable excipients.

In some embodiments, provided herein are ophthalmic compositions including at least one compound of the invention, wherein the composition is a liquid which is ophthalmically acceptable.

In some embodiments, provided herein are methods for the treatment of an ophthalmic disease. In some embodiments, the disease is selected from the group consisting of glaucoma, ocular hypertension, and macular degeneration. Such methods can be performed, for example, by administering to a subject in need thereof a therapeutically effective amount of at least one compound of the invention.

In some embodiments, provided herein are methods for reducing intraocular pressure. Such methods can be performed for example, by administering to a subject in need thereof a therapeutically effective amount of at least one compound of the invention.

In a further embodiment there are provided methods for reducing corneal thickening. Such methods can be performed for example, by administering to a subject in need thereof a therapeutically effective amount of at least one compound of the invention.

Exemplary compounds contemplated for use in the practice of the invention include, but are not limited to, compounds having any one of the structures:

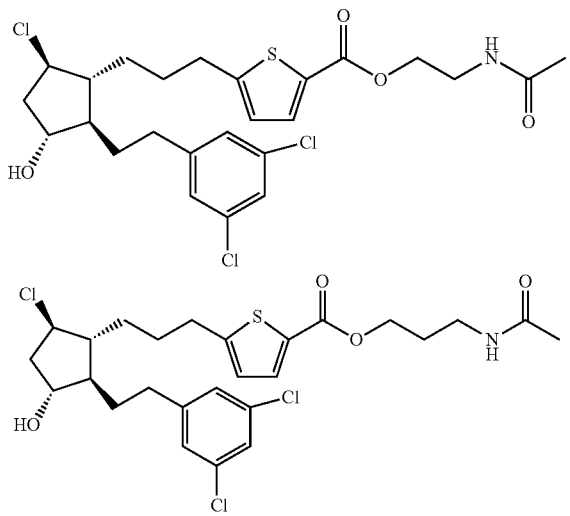

-continued

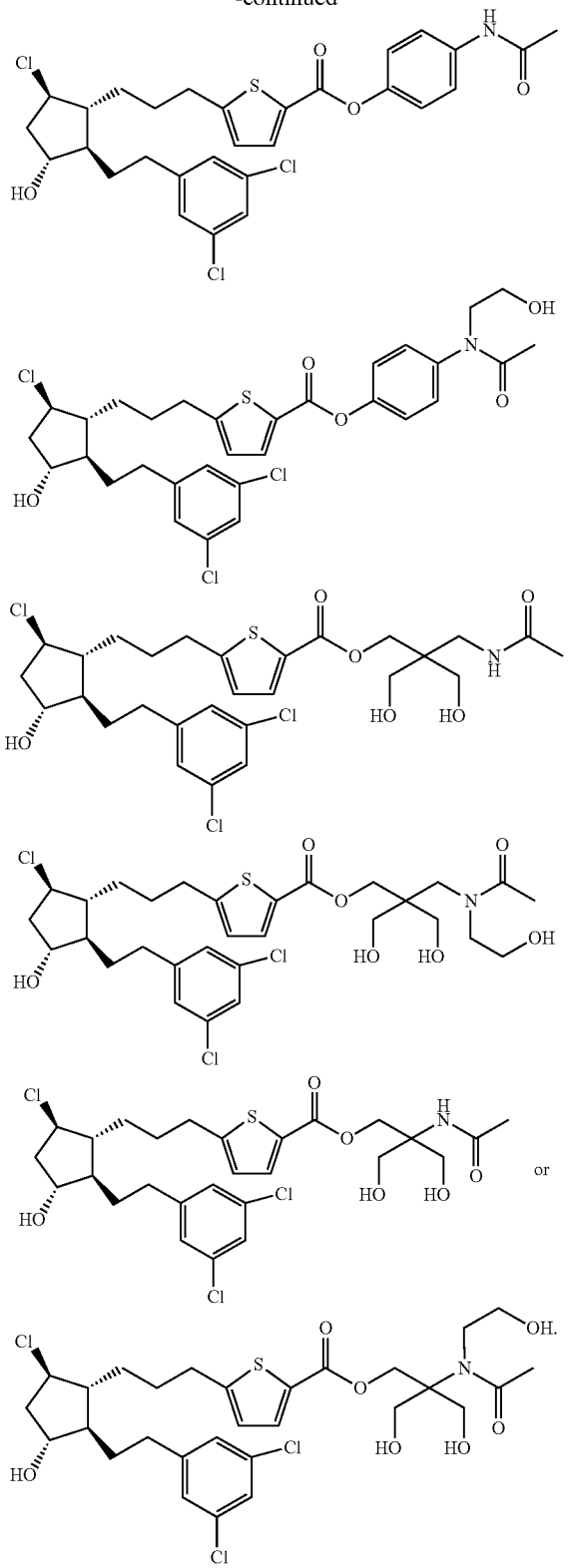

In some embodiments, the compounds provided herein may exist in salt forms, such that the corresponding anions or cations may form a pharmaceutically acceptable salt, such as for example, hydrochloride, hydrobromide, hydroiodide, sulfate, bisulfate, phosphate or acid phosphate, acetate, maleate, fumarate, oxalate, lactate, tartrate, citrate, gluconate, saccharate, p-toluenesulfonate salts, or other anionic counter-ions; or sodium, potassium, ammonium or other cationic counter-ions.

A "pharmaceutically acceptable salt" may be any salt which retains the activity of the parent compound and does not impart any deleterious or untoward effect on the subject to which it is administered and by the context in which it is administered.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring. (See, e.g., *Handbook of Pharmaceutical Salts*, P. Heinrich Stahl & Camille G. Wermuth (Eds), Verlag; *Helvetica Chimica Acta-Zürich*, 2002, 329-345.) The term "pharmaceutically acceptable salt" is also meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66:1-19). Certain specific compounds of the present invention may contain both basic and acidic functionalities that allow the compounds to be converted into either base or acid addition salts.

The invention also relates to pharmaceutical compositions including at least one compound of the invention, the compound being alone or in combination with one or more pharmaceutically acceptable excipients. The invention also relates to methods for the treatment of glaucoma or ocular hypertension. Such methods can be performed, for example, by administering to a subject in need thereof an ophthalmically acceptable pharmaceutical composition containing a therapeutically effective amount of at least one compound of the invention.

Subject compounds can also be used for growing hair, including one or more of: increasing the number of individual hairs, increasing the length of individual hairs, and increasing the width or thickness of individual hairs. Subject compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

Those skilled in the art will readily understand that for administration or the manufacture of medicaments, subject compounds can be admixed with pharmaceutically acceptable excipients. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Liquid pharmaceutically administrable dosage forms can, for example, comprise a solution or suspension of one or more of the subject compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. The composition of the formulation to be administered, in any event, contains a quantity of one or more of the subject compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the subject compound or compounds administered is dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the subject compounds may be in the range of about 0.5 or about 1 to about 100 mg/kg/day.

An ophthalmically acceptable pharmaceutical composition is one that can be administered topically to the eye of a subject in need thereof. Comfort to the subject being administered the composition should be maximized, but other considerations, such as drug stability, may necessitate a pharmaceutical composition that provides less than optimal comfort. In such a case, the composition should be formulated such that it is tolerable to a subject being administered the composition topically.

The pharmaceutical composition can be administered topically in the form of solutions or suspensions, ointments, gels, creams, etc. A "pharmaceutically acceptable excipient" is one that is compatible with the active ingredient of the composition and not harmful to the subject being administered the pharmaceutical composition. Solutions for ophthalmic application are often prepared using physiological saline as a major vehicle. Other vehicles include polyvinyl alcohol, povidone, hydroxypropyl methyl cellulose, poloxamers, carboxymethyl cellulose, hydroxyethyl cellulose, and purified water. Examples of useful excipients also include preservatives, buffers, other pH adjustors, tonicity adjustors, surfactants, antioxidants, and chelating agents.

Useful preservatives include benzalkonium chloride, chlorobutanol, thimerosal, phenylmercuric acetate and phenylmercuric nitrate. Examples of buffers include phosphate, borate, sulfate, acetate, and citrate buffers. Acids or bases may be used to adjust the pH of the compositions as needed. Examples of tonicity agents include glycerin, mannitol, sodium chloride and potassium chloride. Useful surfactants include, for example, Tween 80. Examples of ophthalmically acceptable antioxidants include sodium metabisulfite, sodium thiosulfate, acetylcysteine, butylated hydroxyanisole and butylated hydroxytoluene. A useful chelating agent is edetate disodium.

Mixtures of two or more of any suitable excipients may be used. The aforementioned examples are not intended to limit the scope of the invention in any way. In some embodiments, the ingredients are used in the following amounts:

| Ingredient | Amount (Weight/Volume Percentage) |
| --- | --- |
| active ingredient | About 0.001-5 |
| preservative | 0-0.10 |
| vehicle | 0-40 |
| tonicity adjustor | 1-10 |
| buffer | 0.01-10 |
| pH adjustor | q.s. pH 4.5-7.5 |
| antioxidant | as needed |
| surfactant | as needed |
| purified water | as needed to make 100% |

A therapeutically effective amount of at least one compound of the invention in the pharmaceutical composition disclosed herein is an amount useful to observe a therapeutic effect as compared to a placebo composition that, except for the absence of a compound of the invention, is otherwise identical to the pharmaceutical composition. The amount of at least one compound of the invention to administer depends on factors such as the intended therapeutic effects, the specific mammal in need thereof, the severity and nature of the mammal's condition, the manner of administration, the potency and pharmacodynamics of the particular compound, and the judgment of the prescribing physician. The therapeutically effective dosage of at least one compound of the invention is preferably in the range of about 0.5 or about 1 to about 100 mg/kg/day.

Also, an ophthalmically acceptable pharmaceutical composition should be packaged for single use, or contain a preservative to prevent contamination over multiple uses.

Aside from topical application to treat diseases affecting the eye including glaucoma, pharmaceutical compositions containing at least one compound of the invention can also be administered periocularly, intraocularly, or by other effective means available in the art.

Persons skilled in the art would readily understand that a drug containing one or more of the compounds disclosed herein can be confected as a powder, pill, tablet or the like, or as a solution, emulsion, suspension, aerosol, syrup or elixir suitable for oral or parenteral administration or inhalation. For solid dosage forms or medicaments, non-toxic solid excipients for admixture with compounds disclosed herein include, but are not limited to, pharmaceutical grades of mannitol, lactose, starch, magnesium stearate, sodium saccharin, polyalkylene glycols, talcum, cellulose, glucose, sucrose, and magnesium carbonate. The solid dosage forms may be coated by a material such as glyceryl monostearate or glyceryl distearate, which is utilized in known techniques to delay disintegration and absorption in the gastrointestinal tract for the purpose of providing a sustained action over a longer period. Solid dosage forms may also be coated by the techniques described in U.S. Pat. Nos. 4,256,108, 4,166,452 and 4,265,874 to form osmotic therapeutic tablets for control release.

Pharmaceutically administrable liquid dosage forms can, for example, comprise a solution or suspension of at least one of the compounds disclosed herein and optional pharmaceutical adjutants in a carrier, such as water, saline, aqueous dextrose, glycerol, ethanol and the like. The liquid dosage forms may also contain nontoxic auxiliary substances such as wetting or emulsifying agents, pH buffering agents and the like. Examples of such auxiliary agents include sodium acetate, sorbitan monolaurate, triethanolamine, sodium acetate, triethanolamine oleate, etc. Methods for preparing such dosage forms are well-known to persons skilled in the art (see, for example, Remington's Pharmaceutical Sciences, Mack Publishing Company, Easton, Pa., 16$^{th}$ Edition, 1980).

Parenteral administration is generally characterized by subcutaneous, intramuscular, or intravenous injection. Injectables can be prepared as liquid solutions or suspensions, solid forms that can be reconstituted into solutions or suspensions prior to injection, or as emulsions. Suitable excipients include water, saline dextrose, glycerol, ethanol and the like. Such injectable pharmaceutical compositions may also contain minor amounts of non-toxic auxiliary substances such as wetting or emulsifying agents, pH buffers and the like. Examples mentioned herein are not intended to limit the scope of the invention in any way.

In some embodiments, the subject compounds can be useful in the treatment of baldness and/or hair loss. Alopecia (baldness) is a deficiency of either normal or abnormal hair, and is primarily a cosmetic problem in humans. It is a deficiency of terminal hair, the broad diameter, colored hair that is readily seen. However, in the so-called bald person, although there is a noticeable absence of terminal hair, the skin does contain vellus hair, which is a fine colorless hair which may require microscopic examination to determine its presence. This vellus hair is a precursor to terminal hair.

The subject compounds can be used to stimulate, such as the conversion of vellus hair to growth as terminal hair, as well as increasing the rate of growth of terminal hair.

The subject compounds can also be used to stimulate growth of eye lashes. Application of a subject compound to an eye or an eyelid can result in lashes that are longer and have a fuller, denser appearance in the treated eye. The changes in the lashes may be apparent on gross inspection. Possible changes to lashes can include increased length of lashes, increased number of lashes along the normal lash line, increased thickness and luster of lashes, increased auxiliary lash-like terminal hair in transitional areas adjacent to areas of normal lash growth, increased auxiliary lash-like terminal hairs at the medial and lateral canthal area, increased pigmentation of the lashes, increased numbers, increased length, as well as increased luster, and thickness of fine hair on the skin of the adjacent lid, and finally, increased perpendicular angulation from the skin surface.

In one embodiment, the subject compound is mixed with a dermatologically compatible vehicle or carrier. The vehicle, which may be employed for preparing compositions as described herein, may comprise, for example, aqueous solutions such as e.g., physiological salines, oil solutions, or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, dermatological compositions can be formulated for topical treatment for the stimulation of hair growth which comprises an effective hair growth simulating amount of one or more subject compounds and a dermatologically compatible carrier. Effective amounts of the subject compounds may be determined by one of ordinary skill in the art, but will vary depending on the compound employed, frequency of application and desired result. The subject compound will generally range from about 0.0000001 to about 50% by weight; about 0.001 to about 50% by weight; or about 0.1 to about 30% by weight of the dermatological composition.

In one embodiment, the application of the subject compounds for stimulation of hair growth finds applications in mammalian species, including both humans and animals. In humans, the subject compounds can be applied for example, to the scalp, face beard, head, pubic area, upper lip, eyebrows, and eyelids. In animal raised for their pelts, e.g., mink, the subject compounds can be applied over the entire surface of the body to improve the overall pelt for commercial reasons. The process can also be used for cosmetic reasons in animals, e.g., applied to the skin of dogs and cats having bald patches due to mange or other diseases causing a degree of alopecia.

The pharmaceutical compositions contemplated for the stimulation of hair growth include pharmaceutical compositions suited for topical and local action. The term "topical" as employed with respect to hair growth relates to the use of a subject compound incorporated in a suitable pharmaceutical carrier, and applied at the site of thinning hair or baldness for exertion of local action. Accordingly, such topical compositions include those pharmaceutical forms in which the subject compound is applied externally by direct contact with the skin to be treated.

Conventional pharmaceutical forms for this purpose include ointments, liniments, creams, shampoos, lotions, pastes, jellies, sprays, aerosols, and the like, and may be applied in patches or impregnated dressings depending on the part of the body to be treated. The term "ointment" embraces formulations (including creams) having oleaginous, water-soluble and emulsion-type bases, e.g., petrolatum, lanolin, polyethylene glycols, as well as mixtures of these.

Typically, the subject compounds can be applied repeatedly for the sustained period of time topically on the part of the body to be treated, for example, the eyelids, eyebrows, skin or scalp. The preferred dosage regimen will generally involve regular, such as daily, administration for a period of treatment of at least one month, at least three months, or at least six months.

For topical use on the eyelids or eyebrows, the subject compounds can be formulated in aqueous solutions, creams, ointments, or oils exhibiting physiologically acceptable osmolarity by addition of pharmaceutically acceptable buffers and salts. such formulations may or may not, depending on the dispenser, contain preservatives such as benzalkonium chloride, chlorhexidine, chlorobutanol, parahydroxybenzoic acids and phenylmercuric salts such as nitrate, chloride, acetate, and borate, or antioxidants, as well as additives like EDTA, sorbitol, boric acid and the like as additives. Furthermore, particularly aqueous solutions may contain viscosity increasing agents such as polysaccharides, e.g., methylcellulose, mucopolysaccharides, e.g., hyaluronic acid and chondroitin sulfate, or poly alcohol, e.g., polyvinylalcohol. Various slow releasing gels and matrices may also be employed as well as soluble and insoluble ocular inserts, for instance, based on substances forming in situ gels. Depending on the actual formation and compound to be used, various amounts of the drug and different dose regimens may be employed. Typically, the daily amount of subject compound for treatment of the eyelid may be about 0.1 ng to about 100 mg per eyelid.

For topical use on the skin and scalp, the subject compound can be advantageously formulated using ointments, creams, liniments or patches as a carrier of the active ingredient. Also, these formulations may or may not contain preservatives, depending on the dispenser and nature of use. Such preservatives include those mentioned above, and methyl-, propyl-, or butyl-parahydroxybenzoic acid, betaine, chlorhexidine, benzalkonium chloride, and the like. Various matrices for the slow release delivery may also be used. Typically, the dose to be applied on the scalp is in the range of about 0.1 ng to about 100 mg per day, about 1 ng to about 10 mg per day, or about 10 ng to about 1 mg per day depending on the subject compound and the formulation. To achieve the daily amount of medication depending on the formulation, the subject compound may be administered once or several times daily with or without antioxidants.

For the treatment of glaucoma, combination treatment with the following classes of drugs are contemplated:
β-Blockers (or β-adrenergic antagonists) including carteolol, levobunolol, metipranolol, timolol hemihydrate, timolol maleate, β1-selective antagonists such as betaxolol, and the like, or pharmaceutically acceptable salts or prodrugs thereof;
Adrenergic Agonists including non-selective adrenergic agonists such as epinephrine borate, epinephrine hydrochloride, and dipivefrin, and the like, or pharmaceutically acceptable salts or prodrugs thereof; and
α$_2$-selective adrenergic agonists such as apraclonidine, brimonidine, and the like, or pharmaceutically acceptable salts or prodrugs thereof;
Carbonic Anhydrase Inhibitors including acetazolamide, dichlorphenamide, methazolamide, brinzolamide, dorzolamide, and the like or pharmaceutically acceptable salts or prodrugs thereof;
Cholinergic Agonists Including:
direct acting cholinergic agonists such as carbachol, pilocarpine hydrochloride, pilocarbine nitrate, pilocarpine, and the like, or pharmaceutically acceptable salts or prodrugs thereof;
chlolinesterase inhibitors such as demecarium, echothiophate, physostigmine, and the like, or pharmaceutically acceptable salts or prodrugs thereof;
Glutamate Antagonists and other neuroprotective agents such as Ca$^{2+}$ channel blockers such as memantine, amantadine, rimantadine, nitroglycerin, dextrophan, detromethorphan, CGS-19755, dihydropyridines, verapamil, emopamil, benzothiazepines, bepridil, diphenylbutylpiperidines, diphenylpiperazines, HOE 166 and related drugs, fluspirilene, eliprodil, ifenprodil, CP-101,606, tibalosine, 2309BT, and 840S, flunarizine, nicardipine, nifedimpine, nimodipine, barnidipine, verapamil, lidoflazine, prenylamine lactate, amiloride, and the like, or pharmaceutically acceptable salts or prodrugs thereof;
Prostamides such as bimatoprost, or pharmaceutically acceptable salts or prodrugs thereof; and
Prostaglandins including travoprost, UFO-21, chloprostenol, fluprostenol, 13,14-dihydro-chloprostenol, isopropyl unoprostone, latanoprost and the like.
Cannabinoids including CB1 agonists such as WIN-55212-2 and CP-55940 and the like, or pharmaceutically acceptable salts or prodrugs thereof.

EXAMPLES

The examples provided herein are intended only to illustrate the invention and should in no way be construed as limiting the invention. The following synthetic examples are generally applicable for the preparation of compounds within the scope of formula (I), include those specifically described above, as provided herein.

For example, compounds provided herein may be prepared from acid (1) according to Scheme 1 below.

Scheme 1:

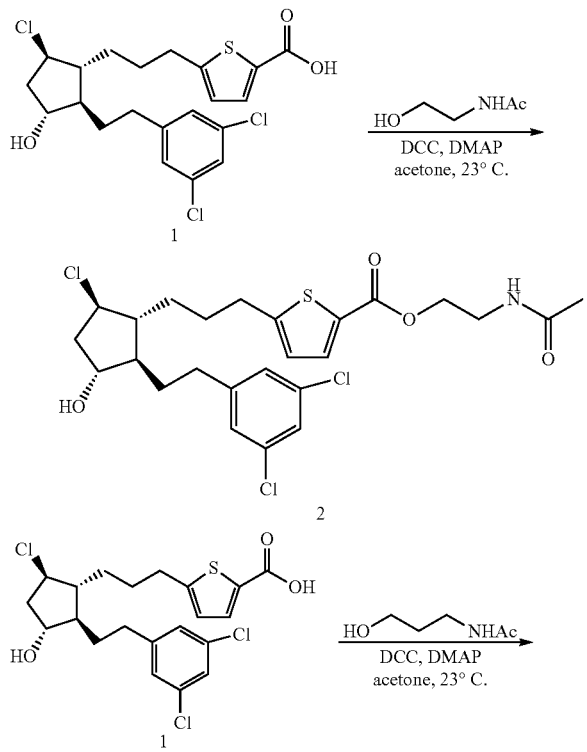

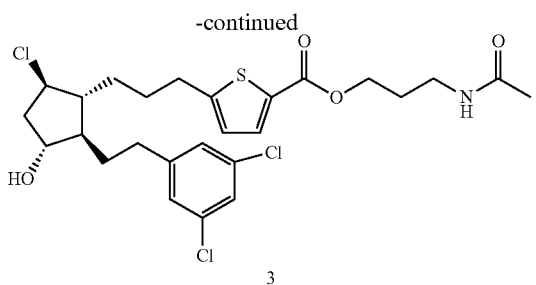

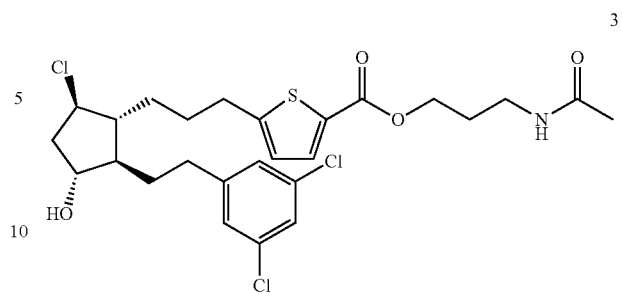

2-Acetamidoethyl 5-(3-((1R,2R,3R,5R)-5-chloro-2-(3,5-dichlorophenethyl)-3-hydroxycyclopentyl)propyl)thiophene-2-carboxylate (2)

Acid 1 is prepared as described in U.S. Pat. No. 7,592,366, the entirety of which is hereby incorporated by reference.

To a solution of acid 1 (80 mg, 0.173 mmol), DMAP (71.8 mg, 0.588 mmol) and 2-acetamidoethanol (0.064 ml, 0.693 mmol) in acetone (4.0 ml) was added N,N'-dicyclohexylcarbodiimide (DCC, 39.3 mg, 0.190 mmol) and the reaction mixture was stirred at room temperature for 24 hours. The precipitated urea was filtered off and the filtrate was concentrated in vacuo. The residue was taken up in EtOAc, washed with water, saturated aqueous sodium chloride, dried over anhydrous MgSO₄, filtered, and concentrated in vacuo. Purification of the residue by flash column chromatography (silica gel 60, 230-400 mesh, 100% EtOAc) afforded 33.3 mg (35%) of ester 2 as a clear, viscous oil. MS (APCI+): 548.

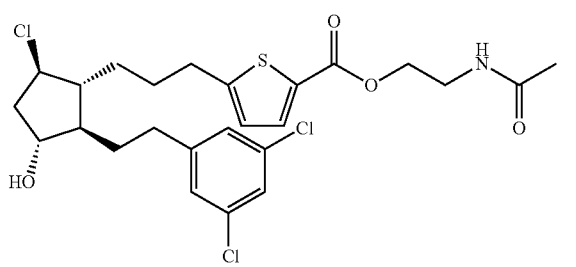

3-Acetamidopropyl 5-(3-((1R,2R,3R,5R)-5-chloro-2-(3,5-dichlorophenethyl)-3-hydroxycyclopentyl)propyl)thiophene-2-carboxylate (3)

To a solution of acid 1 (40 mg, 0.087 mmol), DMAP (36.1 mg, 0.296 mmol) and N-(3-hydroxypropyl)acetamide (0.03 ml, 0.26 mmol) in acetone (2.0 ml) was added N,N'-dicyclohexylcarbodiimide (DCC, 19.8 mg, 0.096 mmol) and the reaction mixture was stirred at room temperature for 24 hours. The precipitated urea was filtered off and the filtrate was concentrated in vacuo. The residue was taken up in EtOAc, washed with water, saturated aqueous sodium chloride, dried over anhydrous MgSO₄, filtered, and concentrated in vacuo. Purification of the residue by flash column chromatography (silica gel 60, 230-400 mesh, 100% EtOAc) afforded 24.9 mg (51%) of ester 3 as a clear, viscous oil. MS (APCI+): 562.

TABLE 1

Exemplary Formulation Vehicle Compositions

| Ingredients (% w/w) | |
|---|---|
| Invention Compound(s) | 0.0005% w/w (5 ppm) |
| Sodium Phosphate Dibasic Heptahydrate | 0.34 |
| Citric acid Monohydrate | 0.072 |
| Sodium Chloride | 0.82 |
| Polysorbate 80 (super refine) | 0.5 |
| NaOH/HCL (1N) | Adjust to pH 6 |
| Purified water | q s |

TABLE 2

Aqueous Stability

| Formulation conc. 0.0005% w/v (5 ppm) in pH 6 buffer contain 1% PS80 Time (days) | % Remaining | |
|---|---|---|
| | Compound 2 | Compound 3 |
| 25° C. (n = 1) | | |
| 14 | 99.3 | 99.2 |
| 28 | 99.6 | 103.5 |
| 40° C. (n = 1) | | |
| 14 | 99.1 | 99.8 |
| 28 | 99.5 | 100.5 |
| 60° C. (n = 1) | | |
| 14 | 98.6 | 99.4 |
| 28 | 97.0 | 98.6 |

As can be seen from the data above, the compounds of the invention exhibit substantial aqueous stability, thereby allowing these compounds to be formulated as aqueous solutions for the treatment of ocular conditions.

Throughout this specification reference is made to publications such as US and foreign patent applications, journal articles, book chapters, and others. All such publications are expressly incorporated by reference in their entirety, including supplemental/supporting information sections published with the corresponding references, for all purposes unless otherwise indicated. To the extent that any recitations in the incorporated references conflict with any recitations herein, the recitations herein will control.

While this invention has been described with respect to these specific examples, it is understood that other modifications and variations are possible without departing from the spirit of the invention.

What is claimed is:

1. A compound of the formula (I), or a pharmaceutically acceptable salt thereof:

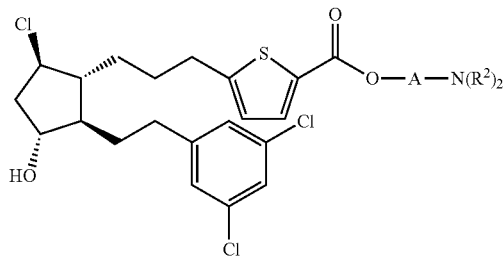

(I)

wherein:
- A is $(C(R^1)_2)_n$, aryl, or heteroaryl containing 1 to 4 heteroatoms selected from the group consisting of N, O and S;
- each $R^1$ is independently selected from the group consisting of H and —$CH_2OH$;
- each $R^2$ is independently selected from the group consisting of H, $C_1$ to $C_6$ alkylhydroxy, and $C(O)R^3$;
- each $R^3$ is independently $C_1$ to $C_6$ alkyl; and
- n is 1 to 6.

2. The compound of claim 1 wherein one $R^2$ is H or alkylhydroxy and the other $R^2$ is $C(O)R^3$.

3. The compound of claim 1, wherein one $R^2$ is H the other $R^2$ is $C(O)R^3$.

4. The compound of claim 1, wherein one $R^2$ is $C_2$ alkylhydroxy and the other $R^2$ is $C(O)R^3$.

5. The compound of claim 2, wherein $R^3$ is methyl.

6. The compound of claim 1, wherein each $R^1$ is —$CH_2OH$.

7. The compound of claim 1, wherein A is aryl and aryl is phenyl.

8. The compound of claim 1, wherein A is $(C(R^1)_2)_n$ and n is 2.

9. The compound of claim 8, wherein each $R^1$ is H.

10. The compound of claim 8, wherein each $R^1$ is —$CH_2OH$.

11. The compound of claim 1, wherein A is aryl and aryl is phenyl.

12. The compound of claim 1, wherein the compound is selected from the group consisting of:

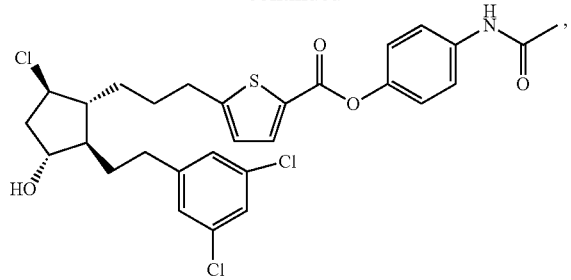

-continued

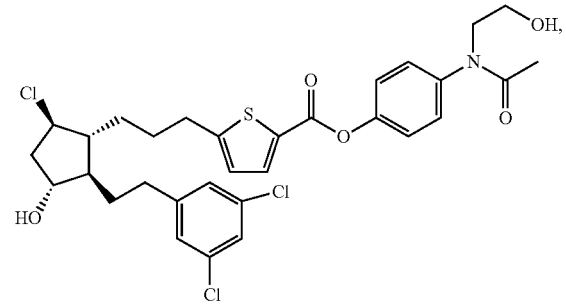

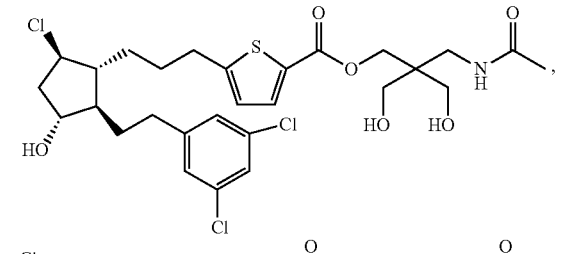

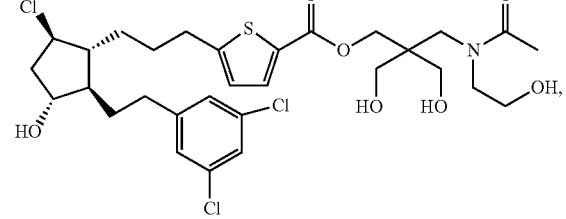

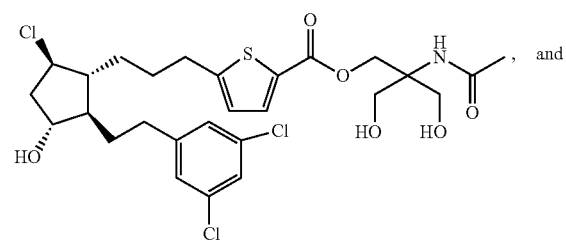

, and

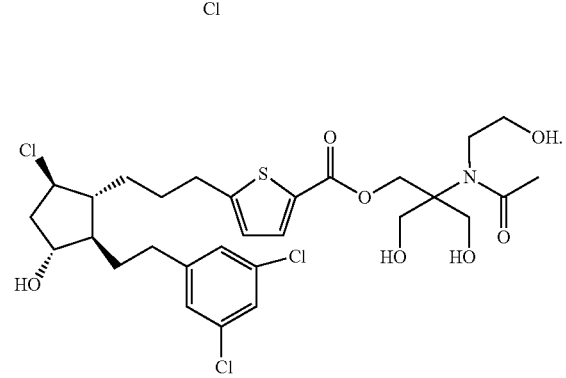

13. A compound of claim 1, wherein the compound is:

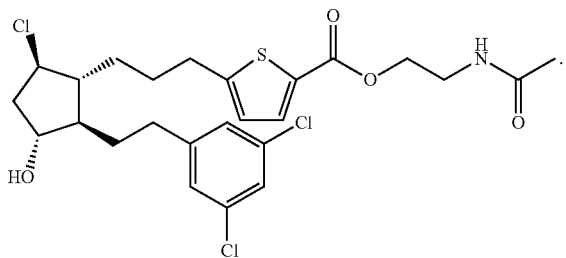 [SMILES: CC(=O)NCCOC(=O)c1ccc(CCC[C@@H]2[C@@H](CCc3cc(Cl)cc(Cl)c3)[C@H](O)C[C@H]2Cl)s1]

14. A compound of claim 1, wherein the compound is:

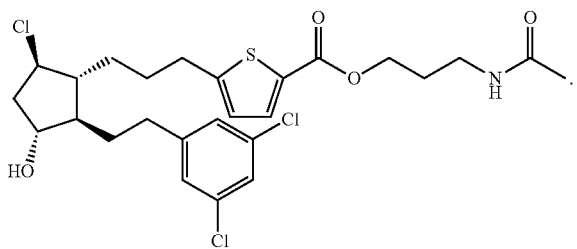 [SMILES: CC(=O)NCCCOC(=O)c1ccc(CCC[C@@H]2[C@@H](CCc3cc(Cl)cc(Cl)c3)[C@H](O)C[C@H]2Cl)s1]

15. A pharmaceutical composition comprising a compound of claim 1, the compound being present alone or in combination with one or more pharmaceutically acceptable excipients.

16. A pharmaceutical composition comprising a compound of claim 1, wherein the composition is a liquid which is ophthalmically acceptable.

17. A method for the treatment of an ophthalmic disease in a human comprising administering to a subject in need thereof a therapeutically effective amount of a compound of claim 1 or pharmaceutical composition of comprising a compound of claim 1.

18. The method of claim 17 wherein the ophthalmic disease is selected from the group consisting of glaucoma, ocular hypertension, and macular degeneration.

19. A method of reducing intraocular pressure comprising administering to a subject in need thereof a therapeutically effective amount of a compound of claim 1 or pharmaceutical composition comprising a compound of claim 1.

20. The method of claim 19 wherein the subject is human.

* * * * *

UNITED STATES PATENT AND TRADEMARK OFFICE
CERTIFICATE OF CORRECTION

| | |
|---|---|
| PATENT NO. | : 9,573,926 B2 |
| APPLICATION NO. | : 14/719750 |
| DATED | : February 21, 2017 |
| INVENTOR(S) | : Robert M. Burk et al. |

It is certified that error appears in the above-identified patent and that said Letters Patent is hereby corrected as shown below:

On the Title Page

In item (74), in Column 2, in "Attorney, Agent or Firm", Line 1, delete "Jonathon" and insert -- Jonathan --, therefor.

In the Specification

In Column 1, Line 42, delete "pupilary" and insert -- pupillary --, therefor.

In Column 3, Line 11, delete "meaning" and insert -- meaning. --, therefor.

In Column 8, Line 50, delete "galactunoric" and insert -- galacturonic --, therefor.

In Column 13, Line 48, delete "metiparanolol," and insert -- metipranolol, --, therefor.

In Column 13, Line 65, delete "pilocarbine" and insert -- pilocarpine --, therefor.

In Column 14, Line 1, delete "chlolinesterase" and insert -- cholinesterase --, therefor.

In Column 14, Line 6, delete "dextrophan," and insert -- dextrorphan, --, therefor.

In Column 14, Line 7, delete "detromethorphan," and insert -- dextromethorphan, --, therefor.

In Column 14, Line 12, delete "nifedimpine," and insert -- nifedipine, --, therefor.

In the Claims

In Column 17, Line 15, in Claim 1, delete "$(C(R^1)_2)_n,$" and insert -- $(C(R^1)_2)_n,$ --, therefor.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*